United States Patent [19]

Johnson et al.

[11] 4,228,169
[45] Oct. 14, 1980

[54] 1,9-DIHYDROXYOCTAHYDROBENZO[c]-QUINOLINES AND 1-HYDROXYHEXAHYDROBENZO[c]-QUINOLINE-9(8H)-ONES AS ANTIEMETIC AGENTS

[75] Inventors: Michael R. Johnson, Gales Ferry; George M. Milne, Niantic, both of Conn.

[73] Assignee: Pfizer Inc., New York, N.Y.

[21] Appl. No.: 52,324

[22] Filed: Jun. 26, 1979

[51] Int. Cl.² .............. A61K 27/00; A61K 31/47
[52] U.S. Cl. .................. 424/258; 424/248.50; 424/248.51; 424/248.54; 424/248.57
[58] Field of Search ............. 424/248.51, 248.54, 424/248.57, 248.50, 258

[56] References Cited
U.S. PATENT DOCUMENTS 4,087,545  5/1978  Archer .................. 424/283

FOREIGN PATENT DOCUMENTS 854655  11/1977  Belgium .

OTHER PUBLICATIONS

Sallen et al., N. Eng. J. Med. 293, 795 (1975).
Borison et al., N. Eng. J. Med. 298, 1480 (1978).

Primary Examiner—Stanley J. Friedman
Attorney, Agent, or Firm—Connolly and Hutz

[57] ABSTRACT 1,9-Dihydroxyoctahydro[c]quinolines (I) and 1-hydroxyhexahydrobenzo[c]quinoline-9(8H)-ones (II), useful as antiemetic agents and derivatives thereof having the formulae

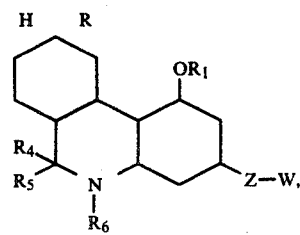

(I)

-continued

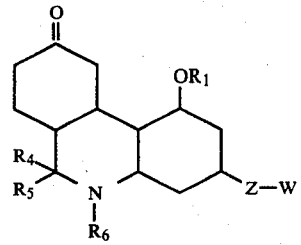

(II)

wherein R is hydroxy or alkanoyloxy having from one to five carbon atoms;
$R_1$ is hydrogen, benzyl, benzoyl, alkanoyl having from one to five carbon atoms or $-CO-(CH_2)_p-NR_2R_3$ wherein p is 0 or an integer from 1 to 4; each of $R_2$ and $R_3$ when taken individually is hydrogen or alkyl having from one to four carbon atoms; $R_2$ and $R_3$ when taken together with the nitrogen to which they are attached form a 5- or 6-membered heterocyclic ring (piperidino, pyrrolo, pyrrolidino, morpholino and N-alkylpiperazino having from one to four carbon atoms in the alkyl group); $R_4$ is hydrogen, alkyl having from 1 to 6 carbon atoms and $-(CH_2)_z-C_6H_5$ wherein z is an integer from 1 to 4; $R_5$ is hydrogen, methyl or ethyl; $R_6$ is hydrogen, $-(CH_2)_y$-carbalkoxy having from 1 to 4 carbon atoms in the alkoxy group wherein y is 0 or an integer from 1 to 4; carbobenzyloxy, formyl, alkanoyl having from two to five carbon atoms, alkyl having from one to six carbon atoms; $-(CH_2)_x-C_6H_5$ wherein x is an integer from 1 to 4; and $-CO(CH_2)_{x-1}-C_6H_5$;
Z is (a) alkylene having from one to nine carbon atoms; (b) $-(alk_1)_m-X-(alk_2)_n-$ wherein each of (alk₁) and (alk₂) is alkylene having from one to nine carbon atoms, with the proviso that the summation of carbon atoms in (alk₁) plus (alk₂) is not greater than 9; each of m and n is 0 or 1; X is O, S, SO or SO₂; and
W is hydrogen, methyl,

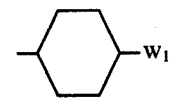

wherein $W_1$ is hydrogen, chloro or fluoro; pyridyl, piperidyl, cycloalkyl having from 3 to 7 carbon atoms, or monosubstituted cycloalkyl wherein the substituent is

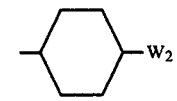

wherein $W_2$ is hydrogen, chloro or fluoro; and pharmaceutically-acceptable acid addition salts of compounds of formulae I and II and the ketals of compounds of formula II wherein the ketal moiety has from two to four carbon atoms.

27 Claims, No Drawings

1,9-DIHYDROXYOCTAHYDROBENZO[c]QUINOLINES AND 1-HYDROXYHEXAHYDROBENZO[c]QUINOLINE-9(8H)-ONES AS ANTIEMETIC AGENTS

BACKGROUND OF THE INVENTION

This invention relates to certain novel benzo[c]quinolines and more particularly to 1,9-dihydroxyoctahydrobenzo[c]quinolines and 1-hydroxyhexahydrobenzo[c]quinolline-9(8H)-ones and derivatives thereof useful as antiemetic agents in mammals, including man.

DESCRIPTION OF THE PRIOR ART

Belgian Pat. No. 854,655, granted Nov. 16, 1977, describes compounds of formulae I and II as CNS agents, especially as analgesics and tranquilizers, as hypotensives, as agents for the treatment of glaucoma and as diuretics, and methods for their preparation.

U.S. Pat. No. 4,087,545 discloses the antiemetic and antinausea properties of 1-hydroxy-3-alkyl-6,6a,7,8,10,-10a-hexahydro-9H-dibenzo[b,d]pyran-9-ones.

Sallan et al. N. E. J. Med. 293, 795 (1975) reported oral Δ9-tetrahydrocannabinol has antiemetic properties in patients receiving cancer chemotherapy.

Δ9-Tetrahydrocannibinol is reported by Shannon et al. (Life Sciences 23, 49–54, 1978) to lack antiemetic effects in apomorphine-induced emeses in the dog. Borison et al., N. England J. of Med. 298, 1480 (1978) report the use of unanesthetized cats as an animal model for determining the antiemetic effect of compounds especially in connection with emesis induced by cancer chemotherapy drugs. They found that pretreatment of unanesthetized cats with 1-hydroxy-3-1',1'-dimethyl-heptyl)-6,6-dimethyl-6,6a,7,8,10,10a-hexahydro-9H-dibenzo[b,d]pyran-9(8H)-one (nabilone) affords pronounced protection against vomiting per se after injection of antineoplastic drugs.

Paton, in *Annual Review of Pharmacology*, 15, 192 (1975) presents generalizations on structure-action relationships among cannabinoids; namely, that the presence of the gem dimethyl group in the pyran ring is critical for cannabinoid activity and substitution of N for O in the pyran ring removes activity.

SUMMARY OF THE INVENTION

It has now been found that certain benzo[c]quinolines; namely, 1,9-dihydroxyoctahydro-6H-benzo[c]quinolines (I) and 1-hydroxyhexahydro-6H-benzo[c]quinoline-9(8H)-ones (II) are effective as antiemetic and antinausea agents against a number of emetic agents via the parenteral and oral routes of administration. They are useful for the treatment and prevention of emesis and nausea in mammals, especially that induced by antineoplastic drugs.

The above-named compounds have the formulae

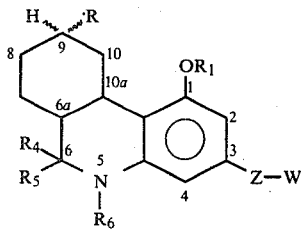

and

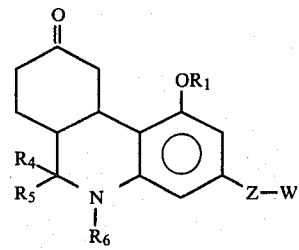

wherein R is selected from the group consisting of hydroxy and alkanoyloxy having from one to five carbon atoms;

$R_1$ is selected from the group consisting of hydrogen, benzyl, benzoyl, alkanoyl having from one to five carbon atoms and —CO—$(CH_2)_p$—$NR_2R_3$ wherein p is 0 or an integer from 1 to 4; each of $R_2$ and $R_3$ when taken individually is selected from the group consisting of hydrogen and alkyl having from one to four carbon atoms; $R_2$ and $R_3$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl groups;

$R_4$ is selected from the group consisting of hydrogen, alkyl having from 1 to 6 carbon atoms and —$(CH_2)_z$—$C_6H_5$ wherein z is an integer from 1 to 4;

$R_5$ is selected from the group consisting of hydrogen, methyl and ethyl;

$R_6$ is selected from the group consisting of hydrogen, —$(CH_2)_y$-carbalkoxy having from one to four carbon atoms in the alkoxy group and y is 0 or an integer from 1 to 4; carbobenzyloxy, formyl, alkanoyl having from two to five carbon atoms, alkyl having from one to six carbon atoms; —$(CH_2)_x$—$C_6H_5$ wherein x is an integer from 1 to 4; and —$CO(CH_2)_{x-1}$—$C_6H_5$;

Z is selected from the group consisting of
(a) alkylene having from one to nine carbon atoms;
(b) —$(alk_1)_m$—X—$(alk_2)_n$— wherein each of $(alk_1)$ and $(alk_2)$ is alkylene having from one to nine carbon atoms, with the proviso that the summation of carbon atoms in $(alk_1)$ plus $(alk_2)$ is not greater that nine; each of m and n is 0 or 1; X is selected from the group consisting of O, S, SO and $SO_2$; and W is selected from the group consisting of hydrogen, methyl, pyridyl, piperidyl,

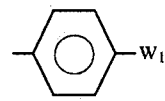

wherein $W_1$ is selected from the group consisting of hydrogen, fluoro, and chloro; and

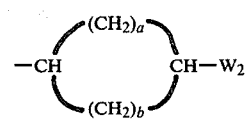

wherein $W_2$ is selected from the group consisting of hydrogen and

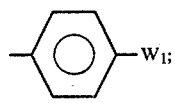

a is an integer from 1 to 5 and b is 0 or an integer from 1 to 5; with the proviso that the sum of a and b is not greater than 5.

Also included in this invention are pharmaceutically acceptable acid addition salts of compounds of formulae I and II. Representative of such salts are mineral acid salts such as the hydrochloride, hydrobromide, sulfate, nitrate, phosphate; organic acid salts such as the citrate, acetate, sulfosalicylate, tartrate, glycolate, malonate, maleate, fumarate, malate, 2-hydroxy-3-naphthoate, pamoate, salicylate, stearate, phthalate, succinate, gluconate, mandelate, lactate and methane sulfonate.

Compounds having formulae I and II above contain asymmetric centers at the 6a- and/or 10a-positions. There may be additional asymmetric centers in the 3-position substituent (—Z—W), and 5-, 6- and 9-positions. Diastereomers with the 9β-configuration are generally favored over the 9α-isomers because of greater (quantitatively) biological activity. For the same reason, the trans(6a,10a)diastereomers of compounds of formula I are generally favored over the cis(6a,10a)diastereomers. As regards compounds of formula II, when one of $R_4$ and $R_5$ is other than hydrogen, the cis-diastereomers are preferred because of their greater biological activity. Among the enantiomers of a given compound, one will generally be favored over the other and the racemate because of its greater activity. For example, the l-enantiomer of 5,6,6aβ,7,8,9,10,10aα-octahydro-1-acetoxy-9β-hydroxy-6β-methyl-3-(5-phenyl-2-pentyloxy)benzo[c]quinoline is favored over the d-enantiomer and the racemate because of its greater antiemetic activity.

Among the 3-position (ZW) diastereoisomers, one will generally be favored over the other. For example, dl-5,6,6aβ,7,8,9α,10,10aα-octahydro-1-acetoxy-9-hydroxy-6β-methyl-3-(1α-methyl-4-phenylbutoxy)benzo[c]quinoline is favored over dl-5,6,6aβ,7,8,9α,10,-10aα-octahydro-1-acetoxy-9-hydroxy-6β-methyl-3-(1β-methyl-4-phenylbutoxy)benzo[c]quinoline and (2'R,6S,6aR,9R,10aR)-(—)-1-acetoxy-5,6,6a,7,8,9,10,-10a-octahydro-9hydroxy-6-methyl-3-(5'-phenyl-2'-pentyloxy)benzo[c]quinoline is favored over (2'S,6S,6aR,9R,10aR)-(—)-1-acetoxy-5,6,6a,7,8,9,10,-10a-octahydro-9-hydroxy-6-methyl-3-(5'-phenyl-2'-pentyloxy)benzo[c]quinoline because of their greater antiemetic activity. For convenience, the above formulae are considered to be generic to and embracive of the racemic modifications of the compounds of this invention, the diastereomeric mixtures, the pure enantiomers and diastereomers thereof. The utility of the racemic mixtures, the diastereomeric mixtures as well as of the pure enantiomers and diastereomers is determined by the biological evaluation described below.

Favored, because of their greater biological activity relative to that of other compounds described herein, are compounds of formulae I and II wherein R is as defined above;

$R_1$ is hydrogen or alkanoyl;
$R_5$ is hydrogen, methyl or ethyl;
and each of $R_4$ and $R_6$ is hydrogen or alkyl;
Z and W have the values shown below:

| Z | m | n | W |
|---|---|---|---|
| alkylene having from 5 to 9 carbon atoms | — | — | H or $CH_3$ |
| alkylene having from 2 to 5 carbon atoms | — | — | $C_6H_5$, 4-$FC_6H_4$, 4-$ClC_6H_4$, 4-pyridyl |
| —(alk$_1$)$_m$—O—(alk$_2$)$_n$— | 1 | 1 | $C_6H_5$, 4-$FC_6H_4$, 4-$ClC_6H_4$, 4-pyridyl |
|  | 0 | 1 |  |
|  | 1 | 0 |  |
| —(alk$_1$)$_m$—O—(alk$_2$)$_n$— | 1 | 1 | H or $CH_3$ |
|  | 0 | 1 | H or $CH_3$ |
|  | 1 | 0 | H or $CH_3$ |

Preferred compounds of formula I are those favored compounds described above wherein R represents hydroxy and which have the trans-configuration.

Especially preferred are those preferred compounds of formulae I and II wherein:
R is hydroxy (formula I only);
$R_1$ is hydrogen or acetyl;
$R_5$ is hydrogen;
$R_4$ is methyl or propyl;
$R_6$ is hydrogen, methyl or ethyl;
when Z is alkylene having from 2 to 5 carbon atoms W is phenyl or pyridyl;
when Z is —(alk$_1$)$_m$—O—(alk$_2$)$_n$— wherein m is 0 and n is 1, (alk$_2$)$_n$ is alkylene having from four to nine carbon atoms, W is hydrogen or phenyl; and
when Z is alkylene having from five to nine carbon atoms, W is hydrogen.

DETAILED DESCRIPTION OF THE INVENTION

The compounds of formulae I and II are prepared according to procedures described in Belgian Pat. No. 854,655. A suitable process begins with appropriately substituted anilines, e.g., 3-hydroxy-5-(Z-W-substituted-)anilines, (III) or derivatives thereof in which the 3-hydroxy group is protected by a group ($Y_1$) easily removable to regenerate the hydroxy group; e.g. methyl, ethyl, benzyl, substituted benzyl wherein the substituent is, for example, alkyl having from 1 to 4 carbon atoms, halo (Cl, Br, F, I), and alkoxy having from one to four carbon atoms. When Z is —(alk$_1$)$_m$—X—(alk$_2$)$_n$—, $Y_1$ is preferably benzyl or a substituted benzyl group since it can subsequently be removed without detriment to the Z group.

The protected aniline derivative (III) is then converted to a compound of formula IV by known technology as described below.

An abbreviated reaction sequence (Flow Sheet A) for preparing representative compounds of formula VIA-C beginning with a 3-(protected hydroxy)-5-(Z-W-substituted)aniline (III) wherein —Z—W is $OCH_3$ is given below.

Flow Sheet A

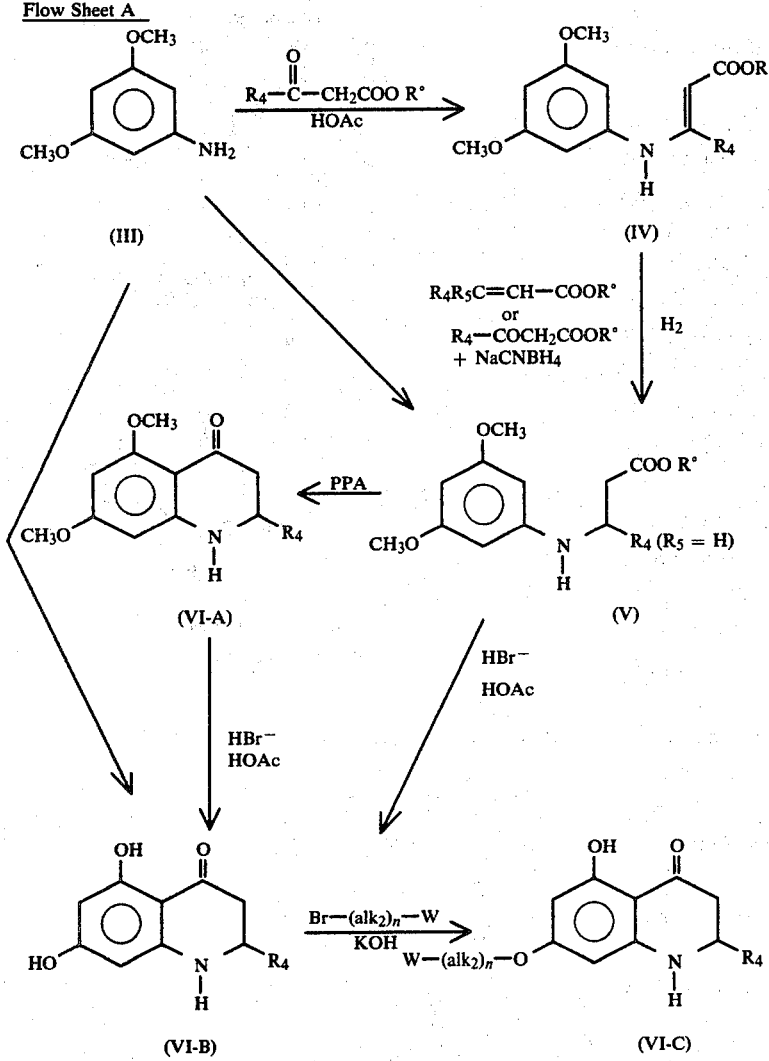

R° in the above flow sheet represents alkyl having from one to six carbon atoms. ($R_5$, for the purpose of illustration in the overall Flow Sheet, is represented as hydrogen. However, in the sequence III→IV or III→ VI-B, $R_5$ can be hydrogen, methyl or ethyl.)

The 5-substituent of formula III compounds can be group —Z—W desired in compounds of formulae II or I, or a group readily convertible to said group. When the Z moiety of group —Z—W is —(alk$_1$)$_m$—X—(alk$_2$)$_n$— wherein X is O or S and each of m and n is 0, the 5-substituent, when W is hydrogen, is —XH (i.e., OH or SH) or a protected —XH group of the formula —X—$Y_1$ wherein $Y_1$ is as defined above. When, of course, —Z—W is —(alk$_1$)$_m$—X—(alk$_2$)$_n$—W wherein m is 1, n is 0 and W is hydrogen, the 5-substituent becomes —(alk$_1$)$_m$—X—H. The —XH group is advantageously protected in the manner described below.

The appropriate 3-(protected hydroxy)-5-substituted anilines are reacted with an alkyl β-ketoester in the presence of acetic acid in a reaction-inert solvent such as benzene or toluene at temperatures of from about 50° C. to the reflux temperature of the solvent under conditions which result in removal of by-product water to provide the corresponding β-[(3-protected hydroxy)-5-substituted anilino]-β-($R_4$)-acrylate (IV).

The alkyl β-anilino-β-($R_4$)-acrylate (IV) is then reduced to the corresponding alkyl-3-[(3-protected hydroxy)-5-substituted anilino]-3-($R_4$)-propionate (V) by, for example, sodium borohydride-acetic acid or catalytic hydrogenation (heterogeneous or homogeneous).

Of course, when the protecting group or groups are benzyl or substituted benzyl, catalytic hydrogenation will result in their removal. For this reason, methyl or ethyl groups are preferred as protecting groups for the 3- and/or 5-hydroxy groups of formula III reactants.

Alternatively, compounds of formula V can be prepared directly from compounds of formula III by reaction of formula III compounds with an alkyl 3,3-$R_4R_5$-acrylate in acetic acid at temperatures ranging from 0° C. to the reflux temperature.

Alternatively, compounds of formula VI-B can be prepared directly by condensation of equimolar quantities of III with the appropriate substituted acrylic acid ($R_4R_5C$=CH—COOH) in pyridine hydrochloride at 150°-200° C.

In addition, when the $R_4,R_5$ groups are both alkyl, treatment of III and the alkyl $R_4,R_5$ acrylate in a reaction-inert solvent, e.g. tetrahydrofuran, with mercuric acetate followed by reduction with sodium borohydride gives V.

Direct conversion of compounds of formula III to compounds of formula V is also conveniently achieved by treating a 3,5-(diprotected hydroxy)aniline hydrochloride with an excess of an alkyl acetoacetate, e.g. ethyl acetoacetate, in the presence of sodium cyanoborohydride in a solvent such as methanol.

The alkyl 3-anilino-3-($R_4$)-propionate (V) is then cyclized to the corresponding 2-($R_4$)-quinolin-4-one (formula VI-A or -B) by means of a suitable cyclizing agent such as polyphosphoric acid (PPA), hydrogen bromide-acetic acid, sulfuric acid, and others known to those skilled in the art.

The ether protecting, or blocking, groups on the 3-(and 5-)hydroxy groups can be removed at the time of cyclization through the use of 48% hydrobromic acid in acetic acid as cyclizing agent and deblocking agent. However, when Z is —(alk$_1$)$_m$—X—(alk$_2$)$_n$— cyclization agents such as polyphosphoric acid or trifluoroacetic acid must be used to avoid cleavage of the ether or thioether linkage. Alternatively, the protecting group (or groups) can be removed subsequent to the cyclization reaction. When the protecting groups are benzyl or substituted benzyl groups, they can be removed by catalytic hydrogenolysis using palladium or platinum supported on carbon or by solvolysis using trifluoroacetic acid. Of course, when group —Z—W contains sulfur, acid debenzylation rather than catalytic debenzylation is used.

Group $R_6$, if not already present in compounds of formula VI-A-C, can be introduced into said compounds by reaction with the appropriate Cl-$R_6$ or Br-$R_6$ reactant according to known procedures. Of course, when an acyl, e.g. acetyl, group $R_6$ is desired in products of formulae I or II, such groups are generally introduced at that point in the reaction sequence (Flow Sheet B) following formation of formula II compounds wherein $R_6$ is hydrogen, e.g., by acylation with the appropriate acyl halide according to known procedures.

Compounds of formula VI and, of course, of formula VI-A-C, are converted by the following illustrative sequence (Flow Sheet B) to representative compounds of formulae II and I ($R_5$ and $R_6$=H in the illustration).

Flow Sheet B

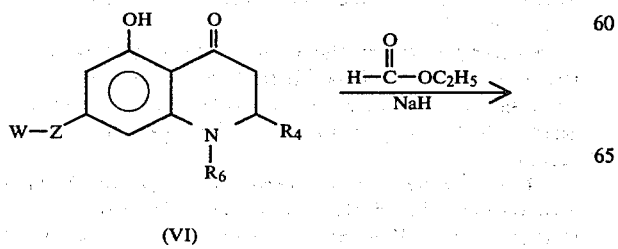

(VI)

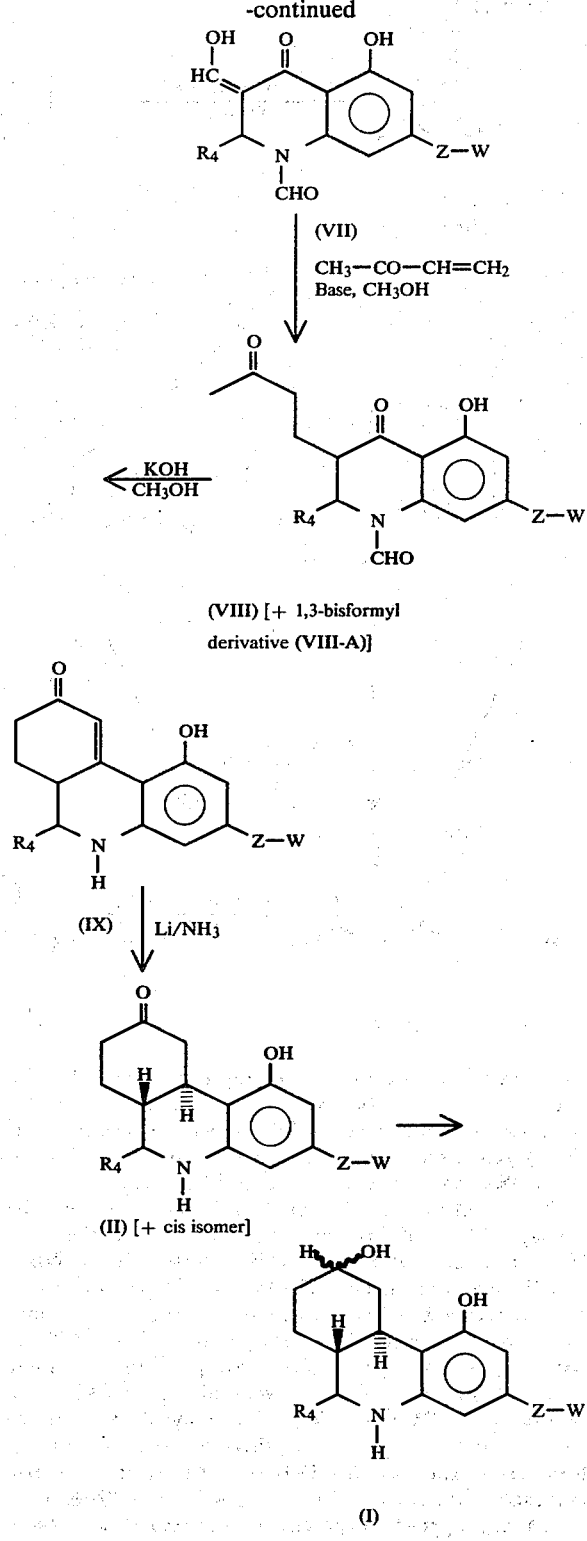

The quinolines of formula VI are converted to hydroxymethylene derivatives of formula VII by reaction with ethyl formate and sodium hydride. The bis-formylated derivative thus produced is treated with methyl vinyl ketone to give a mixture of the corresponding mono-N-formylated Michael adduct (VIII) and 1,3-bis-formylated Michael adduct. The two products are conveniently separated by column chromatography on silica gel.

Aldol condensation of the mono-N-formyl compound of formula VIII affords the enone IX.

The enone (IX) is converted by Birch reduction to a compound of formula II. The Birch reduction is favored because it offers stereoselectivity resulting in formation of the desired trans-ketone of formula II as the major product.

The hydroxy ketones of formula II (compounds wherein $R_1$ is hydrogen) and the dihydroxy compounds of formula I ($R=OR_1=OH$) appear to be rather unstable to oxidation as evidenced by formation of purple to red colors upon standing. They can be stabilized by acylation, particularly acetylation, of the 1-hydroxyl group ($OR_1$) with acetic anhydride in pyridine, and by formation of acid addition salts, e.g., hydrochlorides.

Chemical (sodium borohydride) reduction of the 9-oxo group of compounds of formula II, and preferably, for reasons of stability mentioned above, of the acetylated derivative of formula II, via metal hydride reduction affords compounds of formula I wherein the hydroxyl group at the 1-position is present as its acetylated derivative.

Alternately, and more desirably, compounds of formula IX, especially those wherein the 1-hydroxy group is protected as an ester or benzyl ether, are converted to compounds of formula I by catalytic (Pd/C) hydrogenation.

The acetylated derivatives of formula I thus produced are converted to the corresponding hydroxy derivatives by cleavage of the acetyl group by standard methods.

Esters of compounds of formula II wherein $R_1$ is alkanoyl or $-CO-(CH_2)_p-NR_2R_3$ are readily prepared by reacting formula II compounds with the appropriate alkanoic acid or acid of formula $HOOC-(CH_2)_p-NR_2R_3$ in the presence of a condensing agent such as dicyclohexylcarbodiimide. Alternatively, they are prepared by reaction of a formula II compound with the appropriate alkanoic acid chloride or anhydride, e.g., acetyl chloride or acetic anhydride, in the presence of a base such as pyridine.

Esters of formula I compounds in which each of the R and $R_1$ groups is esterified are prepared by acylation according to the above-described procedures. Compounds in which only the 9-hydroxy group is acylated are obtained by mild hydrolysis of the corresponding 1,9-diacyl derivative, advantage being taken of the greater ease of hydrolysis of the phenolic acyl group. Formula I compounds in which only the 1-hydroxy groups is esterified are obtained by borohydride reduction of the corresponding formula II ketone esterified at the 1-position. The thus-produced formula I compounds bearing 1-acyl-9-hydroxy substitution or 1-hydroxy-9-acyl substitution can then be acylated further with a different acylating agent to produce a diesterified compound of formula I in which the ester groups at the 1- and the 9-positions are different.

The presence of a basic group in the ester moiety ($OR_1$) in the compounds of this invention permits formation of acid-addition salts involving said basic group. When the herein described basic esters are prepared via condensation of the appropriate amino acid hydrochloride (or other acid addition salt) with the appropriate compound of formula I–II in the presence of a condensing agent, the hydrochloride salt of the basic ester is produced. Careful neutralization affords the free base. The free base form can then be converted to other acid addition salts by known procedures.

Acid addition salts can, of course, as those skilled in the art will recognize, be formed with the nitrogen of the benzo[c]quinoline system. Such salts are prepared by standard procedures. The basic ester derivatives are, of course, able to form mono- or di-acid addition salts because of their dibasic functionality.

The antiemetic properties of the compounds of formulae I and II are determined in unanesthetized unrestrained cats according to the procedure described in Proc. Soc. Exptl. Biol. and Med., 160, 437–440 (1979).

The compounds of the present invention are active antiemetics via oral and parenteral administration and are conveniently administered in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, dispersions, solutions, emulsions, syrups and elixirs which may contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial antiemetic dose of drug is administered in an amount effective to prevent nausea. Such dosage in adults may range from 0.01 to 500 mg. per day in single or divided doses. In many instances, it is not necessary to exceed 100 mg. daily. The favored oral dosage range is from about 0.01 to about 300 mg./day; the preferred range is from about 0.10 to about 50 mg./day. The favored parenteral dose is from about 0.01 to about 100 mg./day; the preferred range from about 0.01 to about 20 mg./day.

The compounds (drugs) described herein can be formulated for administration in solid or liquid form for oral or parenteral administration. Capsules containing compounds of formulae I or II are prepared by mixing one part by weight of drug with nine parts of excipient such as starch or milk sugar and then loading the mixture also telescoping gelatin capsules such that each capsule contains 100 parts of the mixture. Tablets are prepared by compounding suitable mixtures of drug and standard ingredients used in preparing tablets, such as starch, binders and lubricants, such that each tablet contains from 0.01 to 100 mg. of drug per tablet.

Suspensions and solutions of these drugs, particularly those wherein $R_1$ (formulae I and II) is hydroxy, are generally prepared just prior to use in order to avoid problems of stability of the drug (e.g. oxidation) or of suspensions or solution (e.g. precipitation) of the drug upon storage. Compositions suitable for such are generally dry solid compositions which are reconstituted for injectable administration.

The examples presented below illustrate the preparation of preferred compounds useful in the process of this invention. They are representative of procedures which can be used to synthesize compounds of formulae I and II described herein.

EXAMPLE 1 dl-5,7-Dihydroxy-2-methyl-4-oxo-1,2,3,4-tetrahydroquinoline

A mixture of 3,5-dimethoxyaniline (4.6 g., 0.03 mole), crotonic acid (2.54 g., 0.03 mole) and pyridine hydrochloride (3.0 g., 1.26 moles) is heated at 185°–200° C. for 45 minutes. The cooled reaction mixture is suspended in water (500 ml.) (pH~3) and the pH adjusted to 7 and the resultant mixture stirred for 10 minutes. The organic layer is separated, dried ($MgSO_4$) and concentrated to 3.2 g. of a yellow oil.

A mixture of glacial acetic acid (110 ml.), 48% hydrobromic acid (110 ml.) and the yellow oil is refluxed for one hour and is then concentrated in vacuo to a dark oil. The oil is dissolved in water and the aqueous solution neutralized to pH 6–7 with 1 N sodium hydroxide. A saturated solution of salt water is added and the resulting mixture extracted with ethyl acetate. The extracts are combined, dried ($MgSO_4$) and concentrated under reduced pressure to a dark oil (2.8 g.). Column chromatography of the crude residue on silica gel using benzene-ether (4:1) as eluant gives an additional 510 mg. of product, m.p. 168°–170° C.

Further purification is achieved by recrystallizing the product from ethyl acetate; m.p. 173°–174° C.

Analysis: Calc'd for $C_{10}H_{11}O_3N$: C, 62.16; H, 5.74; N, 7.25%; Found: C, 62.00; H, 5.83; N, 7.14%.

m/e-193 (m+), 178 (m+-methyl, base peak).

EXAMPLE 2 d,l-5-Hydroxy-2-methyl-7-(5-phenyl-2-pentyloxy)-4-oxo-1,2,3,4-tetrahydroquinoline A mixture of 5-phenyl-2-(R,S)-pentanol (16.4 g., 100 mmole), triethylamine (28 ml., 200 mmole) and dry tetrahydrofuran (80 ml.) under a nitrogen atmosphere is cooled in an ice/water bath. Methanesulfonyl chloride (8.5 ml., 110 mM) in dry tetrahydrofuran (20 ml.) is added dropwise at such a rate that the temperature holds essentially constant. The mixture is allowed to warm to room temperature and is then filtered to remove triethylamine hydrochloride. The filter cake is washed with dry tetrahydrofuran and the combined wash and filtrate evaporated under reduced pressure to give the product as an oil. The oil is dissolved in chloroform (100 ml.) and the solution washed with water (2×100 ml.) and then with saturated brine (1×20 ml.). Evaporation of the solvent affords 21.7 g. (89.7%) yield of the mesylate of d,l-5-phenyl-2-pentanol which is used in the next step without further purification.

A mixture of d,l-5,7-dihydroxy-2-methyl-4-oxo-1,2,3,4-tetrahydroquinoline (114.8 g., 0.594 mole), potassium carbonate (174.8 g., 1.265 moles), N,N-dimethylformamide (612 ml.) and d,l-5-phenyl-2-pentanol mesylate (165.5 g., 0.638 mmole), under a nitrogen atmosphere, is heated to 80°–82° C. in an oil bath for 1.75 hours. The mixture is cooled to room temperature and then poured into ice/water (4 liters). The aqueous solution is extracted with ethyl acetate (2×4 liters) and the combined extracts washed successively with water (4×2 liters) and saturated brine (1×2 liters). The extract is then dried ($MgSO_4$), and evaporated to give the product (196 g.). It is used without further purification.

m/e-339 (m+).

$^1$H NMR (60 MHz) $\beta_{CDCl_3}^{TMS}$ (ppm): 12.73 (s, 1H, OH), 7.22 (s, 5H, aromatic), 5.80 (d, J=3 H$_3$, 1H, meta H), 5.58 (d, J=3 H$_3$, 1H, meta H), 1.25 (d, 6H, $\underline{CH_3}$—CH—N and $\underline{CH_3}$—CH—O—), 1.41–4.81 (m, 11H, remaining protons).

EXAMPLE 3 d,l-1-Formyl-5-hydroxy-3-hydroxymethylene-2-methyl-7-(5-phenyl-2-pentyloxy)-4-oxo-1,2,3,4-tetrahydroquinoline A solution of d,l-5-hydroxy-2-methyl-7-(5-phenyl-2-pentyloxy)-4-oxo-1,2,3,4-tetrahydroquinoline (195 g., ca. 0.58 mole) in ethyl formate (1140 g., 14.6 moles) is added dropwise to sodium hydride (72 g., 3.0 moles, obtained by washing 144 g. of 50% sodium hydride with hexane, 3×500 ml.), with good stirring. After about 1.5 hours when ⅔ of the ethyl formate solution is added, the addition is discontinued to allow the vigorous foaming to subside. Diethyl ether (600 ml.) is added and the mixture stirred for 15 minutes before adding the remainder of the ethyl formate solution. When addition is complete, diethyl ether (600 ml.) is added, the reaction mixture stirred for an additional 10 minutes and then poured onto ice water (2 liters). It is acidified to pH 1 with 10% HCl and the phase separated and extracted with ethyl acetate (2×2 liters), brine (1×one liter) and dried ($MgSO_4$). Concentration gives 231 g. of red-brown oil which is used without further purification.

$R_f$=0.1–0.5 (stretched) on thin layer chromatography, silica gel plates, benzene/ether (1:1).

EXAMPLE 4 d,l-1-Formyl-5-hydroxy-2-methyl-7-(5-phenyl-2-pentyloxy)-4-oxo-3-(3-oxobutyl)-1,2,3,4-tetrahydroquinoline To a solution of d,l-1-formyl-3-hydroxymethylene-5-hydroxy-2-methyl-7-(5-phenyl-2-pentyloxy)-4-oxo-1,2,3,4-tetrahydroquinoline (229 g., ca. 0.58 mole) in methanol (880 ml.) under a nitrogen atmosphere is added triethylamine (27.2 ml.) with stirring. Methyl vinyl ketone (97.0 ml.) is then added and the mixture stirred overnight at room temperature.

The reaction is complete at this point and comprises a mixture of the title compound and d,l-1,3-diformyl-5-hydroxy-2-methyl-7-(5-phenyl-2-pentyloxy)-4-oxo-3-(3-oxobutyl)-1,2,3,4-tetrahydroquinoline. The following steps are required to convert the diformyl compound to the desired title compound.

The reaction mixture is diluted with ether (6 liters) and then washed successively with 10% aqueous sodium carbonate (4×1700 ml.), brine (1×2 liters) and then dried ($MgSO_4$). Concentration of the solution affords 238 g. of a red-brown oil. The oil is dissolved in methanol (1920 ml.) and the solution cooled to 0° C. Potassium carbonate (21.2 g.) is added, the mixture stirred for 3 hours at 0° C. and then treated with acetic acid (18.7 g.). The methanol is removed under reduced pressure and the resultant oil stirred with water (2 liters) and ethyl acetate (2 liters) for 10 minutes. The aqueous phase is separated, extracted with ethyl acetate (1×2 liters) and the combined ethyl acetate solutions washed with water (2×2 liters), brine (1×2 liters) and dried ($MgSO_4$). Concentration under reduced pressure and chromatography of the concentrate on silica gel (1.8 kg.) gives 159 g. of the title product.

m/e-437 (m+).

$^1$H NMR (60 MHz) $\delta_{CDCl_3}^{TMS}$ (ppm): 12.7 (s, 1H, OH), 8.78 (bs, 1H, —CHO), 7.22 (s, 5H, aromatic), 6.22 (bs, 2H, meta H's), 2.12, 2.07 (s, 3H, —$\underline{CH_3}$—CO—), 1.31 (d, 3H, —CH$_3$—C—O—), and 1.57-5.23 (m, 13H, remaining protons).

Similar treatment of 35 g. (0.09 mole) of dl-1-formyl-5-hydroxy-3-hydroxymethylene-2-methyl-7-(4-phenylbutyloxy)-4-oxo-1,2,3,4-tetrahydroquinoline gives 22.7 g. (60%) of dl-1-formyl-5-hydroxy-2-methyl-7-(4-phenylbutyloxy)-4-oxo-3-(3-oxobutyl)-1,2,3,4-tetrahydroquinoline, m.p. 101°-103° C. The analytical sample is obtained by recrystallization from methanol, m.p. 104°-105° C.

Calc'd. for C$_{25}$H$_{29}$O$_5$N: C, 70.90; H, 6.90; N, 3.31%; Found: C, 70.77; H, 6.81; N, 3.46%.

$^1$H NMR (60 MHz) $\delta_{CDCl_3}^{TMS}$ (ppm): 12.88 (s, 1H, —OH), 9.08 (bs, 1H, —CHO), 7.29 (s, 5H, C$_6$H$_5$), 6.25 (bs, 2H, meta H's), 4.88-5.43 (m, 1H, —CHN), 3.86-4.21 (m, 2H, —CH$_2$—O—), ca. 2.49-3.02 [m, 7H, ArCH$_2$, —(CH$_2$)$_2$—C(=O)—, —CH—C(=O)], 2.18 [s, 3H, CH$_3$—C(=O)], 1.68-2.03 [m, 4H, —(CH$_2$)$_2$—], 1.13 (d, 3H, CH$_3$). m/e-423 (m+).

EXAMPLE 5 d,l-5,6,6a,7-Tetrahydro-1-hydroxy-6β-methyl-3-(5-phenyl-2-pentyloxy)benzo[c]quinolin-9(8H)-one A solution of d,l-1-formyl-5-hydroxy-2-methyl-7-(5-phenyl-2-pentyloxy)-4-oxo-3-(3-oxobutyl)-1,2,3,4-tetrahydroquinoline (174 g., 0.398 mole) in methanolic 2 N KOH (5.9 liters) and methanol (5.9 liters) is stirred and heated at reflux overnight under a nitrogen atmosphere. To the cooled solution is added acetic acid (708 g.) dropwise with stirring over a 15 minute period. The resulting solution is concentrated by rotary evaporation (in vacuo, water aspirator) to a semisolid which is filtered and washed first with water to remove potassium acetate and then with ethyl acetate until all the black tar is removed. Yield=68 g. (44%) yellow solids, m.p. 188°-190° C. Recrystallization from hot ethyl acetate affords the pure product, m.p. 194°-195° C.

m/e-391 (m+).

Analysis: Calc'd. for C$_{25}$H$_{29}$O$_3$N: C, 76.09; H, 7.47; N, 3.58%; Found: C, 76.43; H, 7.48; N, 3.58%.

$^1$H NMR (60 MHz) $\delta^{TMS}$ (100 mg. dissolved in 0.3 ml. CD$_3$OD and 0.3 ml. CD$_3$S(O)CD$_3$) (ppm): 7.21 (s, 5H, aromatic), 5.80 (s, 2H, meta H's), 1.20 (d, 6H, CH$_3$—CHO and CH$_3$—CH—N).

From the mother liquors, a small amount of the corresponding axial methyl derivative is obtained upon evaporation. It is purified by column chromatography on silica gel using benzene/ether (1:1) as eluant. Evaporation of the eluate and recrystallization of the residue from ether/hexane (1:1) affords analytically pure material, m.p. 225°-228° C.

Its R$_f$ value upon thin layer chromatography on silica gel using 2.5% methanol in ether as eluant and visualization with fast blue is 0.34. The 6β-methyl derivative exhibits R$_f$=0.41.

m/e-391 (m+).

$^1$H NMR (60 MHz) $\delta^{TMS}$ (100 mg. dissolved in 0.3 ml. CD$_3$OD and 0.3 ml. CD$_3$S(O)CD$_3$) (ppm): 7.19 (s, 5H, aromatic), 5.75 (s, 2H, meta H's), 1.21 (d, 3H, CH$_3$—CHO—), and 0.95 (d, 3H, CH$_3$—CH—N).

EXAMPLE 6 d,l-5,6,6a,7,10,10a-Hexahydro-1-acetoxy-6β-methyl-3-(5-phenyl-2-pentyloxy)benzo[c]-guinolin-9(8H)-one, trans- and cis- isomers Ammonia (1150 ml.) is condensed directly into a flame-dried 3 liter/3 neck flask (under a nitrogen atmosphere) equipped with mechanical stirrer, a 500 ml. dropping funnel and solid CO$_2$/acetone cooling (~ −75° C.). Lithium wire (2.2 g., cut into ¼" pieces) is added and a characteristic blue color forms immediately. To the stirred blue solution at −78° C. is added d,l-5,6,6a,7-tetrahydro-1-hydroxy-6β-methyl-3-(5-phenyl-2-pentyloxy)benzo[c]quinolin-9(8H)-one (21.5 g., 0.055 mole) dissolved in tetrahydrofuran (250 ml.) dropwise over a 10 minute period. After an additional 5 minutes of stirring at −78° C., the reaction mixture is quenched by the addition of dry ammonium chloride (20 g.). The cooling is then discontinued and the reaction mixture warmed slowly on a steam bath to evaporate the ammonia. When almost dry, ethyl acetate (2 liters) and water (1 liter) are added and the mixture stirred for 10 minutes. The layers are then separated and the aqueous phase is extracted once more with ethyl acetate (500 ml.). The combined organic extracts are washed once with water (1 liter), dried (MgSO$_4$) and concentrated to a brown semi-solid (~28 g.). This residue is immediately dissolved in methylene chloride (200 ml.), 4-dimethylaminopyridine (7.5 g., 0.061 mole) and triethylamine (6.1 g., 0.061 mole) added and the stirred solution cooled to 0° C. (ice/water cooling) under a nitrogen atmosphere. Acetic anhydride (6.1 g., 0.061 mole) is then added dropwise over 5 minutes with good stirring. After an additional 30 minutes of stirring at 0° C., the reaction mixture is diluted with ethyl acetate (2 liters) and water (1 liter) and stirred for 10 minutes. The aqueous is extracted once more with water and the combined organics washed successively with water (4×1 liter), saturated sodium bicarbonate (1×1 liter), brine (1×1 liter), dried (MgSO$_4$) and concentrated to a light brown oil (~27 g.). The residue is chromatographed on 1.8 kg. of silica gel using benzene 15/ethyl acetate as the eluting solvent. One liter fractions are collected.

After elution of less polar impurities, fractions 16-20 are combined and evaporated to a residue which is crystallized from ether/petroleum ether to yield 5.6 g. (23.4%) of the trans-isomer of the title product. Fractions 21-27 are combined to give 7.6 g. (31.8%) of a mixture of the trans- and cis-isomers, and fractions 28-32 are combined to give 2.5 g. (10.4%) of the cis-isomer of the title product.

The trans-isomer exhibits the following characteristics:

m/e-435 (m+).

$^1$H NMR (60 MHz) $\delta_{CDCl_3}^{TMS}$ (ppm): 7.24 (s, 5H, aromatic), 5.97 (s, 2H, meta H's), 2.28 (s, 3H, CH$_3$—COO), 1.23 (d, 3H, CH$_3$—CH—O—), 1.20 (d, 3H, CH$_3$—CH—N), 1.3-4.5 (m, 17H, remaining protons).

M.P.-81°-83° C.

Analysis: Calc'd. for C$_{27}$H$_{33}$O$_4$N: C, 74.45; H, 7.64; N, 3.22%; Found: C, 74.15; H, 7.68; N, 3.18%.

The cis-isomer has the following characteristics:

m/e-435 (m+).

M.P. of HCl salt-172°-176° C. (dec.) (from acetone-ether).

Analysis: Calc'd. for C$_{27}$H$_{33}$O$_4$N.HCl: C, 68.71; H, 7.26; N, 2.97%; Found: C, 68.86; H, 7.16; N, 2.97%.

EXAMPLE 7 d,l-trans-5,6,6aβ,7,8,9,10,10aα-octahydro-1-acetoxy-9β-hydroxy-6β-methyl-3(5-phenyl-2-pentyloxy)benzo[c]quinoline Sodium borohydride (7.57 g., 0.20 mole) is added to methanol (200 ml.) under a nitrogen atmosphere and cooled in an acetone/dry ice bath to about −75° C. The mixture is stirred for about 20 minutes to dissolve most, if not all, the sodium borohydride. A solution of d,l-trans-5,6,6aβ,7,10,10aα-hexahydro-1-acetoxy-6β-methyl-3-(5-phenyl-2-pentyloxy)benzo[c]quinolin-9(8H)-one (8.71 g., 0.02 mole) in tetrahydrofuran (88 ml.) is cooled to about −50° C. and then added dropwise over a 5–10 minute period to the sodium borohydride solution. The reaction mixture is stirred at about −70° C. for 30 minutes and is then poured onto a mixture of water (1000 ml.) containing ammonium chloride (45 g., 0.80 mole) crushed ice (250 ml.) and ethyl acetate (250 ml.). The layers are separated and the aqueous extracted with ethyl acetate (3×200 ml.). The combined extracts are washed with water (1×100 ml.) and dried (MgSO$_4$). The dried extract is cooled to about 5° C. A solution of ethyl acetate (15 ml.)/HCl, 1.5 N (0.025 mole) is then added dropwise over a 15 minute period. Upon stirring the mixture at 0°–5° C., the hydrochloride salt of the title product precipitates. The mixture is stirred for a half-hour, filtered and the salt dried at 25° C./0.055 mm. to give 6.378 g. (67.3%) of product, m.p. 195°–198° C. (dec.).

EXAMPLE 8 d,l-cis-5,6,6aβ,7,8,9,10,10aα-octahydro-1-acetoxy-9α-hydroxy-6β-methyl-3-(5-phenyl-2-pentyloxy)benzo[c]quinoline To a solution of d,l-cis-5,6,6aβ,7,10,10aβ-hexahydro-1-acetoxy-6β-methyl-3-(5-phenyl-2-pentyloxy)-benzo[c]quinolin-9(8H)-one (1.0 g., 2.296 mmole) in dry tetrahydrofuran (100 ml.) at −78° C. is added, with stirring, potassium tri-sec-butyl borohydride (4.6 ml., of 0.5 M, 2.296 mmole) dropwise over a period of five minutes. The reaction mixture is stirred an additional 30 minutes at −78° C. and is then poured, with stirring, into a solution of 5% acetic acid (250 ml.) and ether (500 ml.) pre-cooled to 0° C. The layers are separated and the aqueous layer extracted with additional ether (250 ml.). The combined ether extracts are washed successively with water (2×250 ml.), saturated sodium bicarbonate solution (1×250 ml.) and brine (1×250 ml.), dried (MgSO$_4$) and concentrated in vacuo to give a yellow oil (1.4 g.). The crude oil is chromatographed on silica gel (100 g.) using benzene/ether (3:1) as eluant. After elution of less polar impurities, the title compound is isolated as a clear oil (700 mg.). The oil is dissolved in ether (35 ml.) and treated with ether saturated with HCl gas to give the hydrochloride salt of the title compound (448 mg.), m.p. 115°–124° C. after recrystallization from ether/chloroform.

MS (mol. ion)=437.

IR (KBr): 5.58 μ(ester >C=O).

Analysis: Calc'd. for C$_{27}$H$_{35}$O$_4$N.HCl: C, 68.41; H, 7.66; N, 2.96%; Found: C, 68.52; H, 7.91; N, 2.73%.

EXAMPLE 9 d,l-trans-5,6,6aβ,7,8,9,10,10aα-octahydro-1,9-dihydroxy-6β-methyl-3-(5-phenyl-2-pentyloxy)benzo[c]quinoline A solution of 145 mg. d,l-trans-5,6,6aβ,7,8,9,10,10aα-octahydro-1-acetoxy-9-hydroxy-6β-methyl-3-(5-phenyl-2-pentyloxy)benzo[c]quinoline and 46 mg. potassium carbonate in 35 ml. methanol is stirred at room temperature. After 30 minutes, the reaction mixture is neutralized with acetic acid and concentrated under reduced pressure. The residue is dissolved in ether (100 ml.), washed successively with water (2×35 ml.), saturated sodium bicarbonate (1×35 ml.), brine (1×40 ml.), dried (MgSO$_4$) and concentrated under reduced pressure to give d,l-trans-5,6,6aβ,7,8,9,10,10aα-octahydro-1,9-dihydroxy-6β-methyl-3-(5-phenyl-2-pentyloxy)benzo[c]quinoline.

me/-395 (m+).

Conversion to the hydrochloride gives a powder, m.p. 151°–156° C.

IR (KBr): 3.00, 4.00 (HN$^\oplus$=), 6.10 and 6.25μ.

EXAMPLE 10 d,l-trans-5,6,6aβ,7,10,10aα-hexahydro-1-acetoxy-5,6β-dimethyl-3-(5-phenyl-2-pentyloxy)benzo[c]quinolin-9(8H)-one To a stirred solution of 436 mg. of d,l-trans-5,6,6aβ,7,10,10aα-hexahydro-1-acetoxy-6β-methyl-3-(5-phenyl-2-pentyloxy)benzo[c]quinolin-9(8H)-one in 3 ml. acetonitrile cooled to 15° C. is added 0.5 ml. 37% aqueous formaldehyde followed by 100 mg. sodium cyanoborohydride. Acetic acid is added to maintain a neutral pH until the reaction is complete as evidenced by no remaining starting material by thin layer chromatography. The product is isolated in the following manner.

Ice water and ether is added to the reaction mixture, the ether layer separated and the aqueous extracted once more with ether. The combined ether layers are combined, dried and evaporated to yield the desired d,l-trans-5,6,6aβ,7,10,10aα-hexahydro-1-acetoxy-5,6β-dimethyl-3-(5-phenyl-2-pentyloxy)benzo[c]-quinolin-9(8H)-one; an oil.

m/e-449 (m+).

Analysis of hydrochloride Calc'd. for C$_{28}$H$_{35}$O$_4$N.HCl: C, 69.19; H, 7.47; N, 2.88%; Found: C, 68.72; H, 7.18; N, 2.74%.

m.p. 94°–97° as the HCl salt.

Similarly, d,l-cis-5,6,6aβ,7,10,10aα-hexahydro-1-acetoxy-6β-methyl-3-(5-phenyl-2-pentyloxy)benzo[c]quinolin-9(8H)-one is converted to d,l-cis-5,6,6aβ,7,10,10aα-hexahydro-1-acetoxy-5,6β-dimethyl-3-(5-phenyl-2-pentyloxy)benzo[c]quinolin-9(8H)-one, as an oil.

m/e-449.

Analysis: Calc'd. for C$_{28}$H$_{35}$O$_4$N: C, 74.80; H, 7.85; N, 3.12%; Found: C, 74.66; H, 8.05; N, 2.66%.

m.p. 69°–75° C. as the HCl salt.

EXAMPLE 11 d,l-trans-5,6,6aβ,7,8,9,10,10aα-octahydro-1-acetoxy-5,6β-dimethyl-9-hydroxy-3-(5-phenyl-2-pentyloxy)benzo[c]quinoline Formaldehyde (1.1 ml. of 37% aqueous) is added to a solution of d,l-trans-5,6,6aβ,7,10,10aα-hexahydro-1- acetoxy-6β-methyl-3-(5-phenyl-2-pentyloxy)benzo[c]-quinoline-9(8H)-one in acetonitrile (15 ml.) at room temperature, followed by sodium cyanoborohydride (0.262 g.). The reaction mixture is stirred for one hour during which time the pH is maintained at neutral pH by addition of acetic acid as needed. Additional sodium cyanoborohydride (0.262 g.) and methanol (15 ml.) are added to the reaction mixture, which is then acidified to pH 3, stirred for two hours, and concentrated under reduced pressure to an oil. The oil is diluted with water (50 ml.), the pH then adjusted to 9–10 by means of aqueous sodium hydroxide, and the alkaline mixture extracted with ether (3×200 ml.). The combined ether extracts are washed with brine, dried ($Na_2SO_4$) and concentrated under reduced pressure to a clear oil. The oil is then dissolved in 50% ether-hexane and charged to a silica gel column. The column is eluted first with 50% ether-hexane followed by 60%, 70% and 75% etherhexane. The eluate is monitored by thin layer chromatography (ether-10, hexane-1). The first product collected is d,l-trans-5,6,6a,7,10,10a-hexahydro-1-acetoxy-5,6β-dimethyl-3-(5-phenyl-2-pentyloxy)benzo[c]-quinolin-9(8H)-one.

The second product is the 9α-hydroxy diastereomer of the title compound.

The third product is the 9β-hydroxy diastereomer of the title compound:
d,l-trans-5,6,6aβ,7,8,9,10,10aα-octahydro-1-acetoxy-5,6β-dimethyl-9β-hydroxy-3-(5-phenyl-2-pentyloxy)-benzo[c]quinoline, which is isolated as the hydrochloride salt; m.p. 163°–165° C.
m/e−451 (m+).

EXAMPLE 12

(2'R,6S,6aR,9R,10aR)-(−)-1-Acetoxy-5,6,6a,7,8,9,10,-10a-octahydro-9-hydroxy-5,6-dimethyl-3-(5-phenyl-2-pentyloxy)benzo[c]quinoline To a stirred solution of 1.0 g. (0.0021 moles) (2'R,6S,6aR,9R,10aR)-(−)-1-acetoxy-5,6,6a,7,8,9,10,-10a-octahydro-9-hydroxy-6-methyl-3-(5-phenyl-2-pentyloxy)-benzo[c]quinoline hydrochloride in 30 ml. $CHCl_3$ is added 30 ml. saturated $NaHCO_3$ solution, and the mixture stirred 5 minutes at room temperature. The layers are separated and the aqueous layer re-extracted with 20 ml. $CHCl_3$. The combined chloroform layers are dried ($MgSO_4$), filtered and the solvent removed in vacuo to yield the free base as a colorless foam.

This foam is dissolved in 40 ml. tetrahydrofuran and combined with 1.0 g. 5% Pd/C, 1.05 ml. (0.018 moles=8.7 equiv.) glacial acetic acid and 15.8 ml. (0.20 moles=100 equiv.) 37% aqueous formaldehyde. The mixture is placed in a Parr apparatus at 50 p.s.i. and hydrogenated for 50 minutes. The catalyst is filtered through diatomaceous earth, washing well with ethyl acetate. The filtrate is diluted to 150 ml. with ethyl acetate then washed successively 3× with 100 ml. saturated $NaHCO_3$ solution, 75 ml. $H_2O$ 3×, 75 ml. brine 1×, and dried over $MgSO_4$. The solvent is filtered and removed in vacuo yielding a yellow viscous oil which is chromatographed on 50 g. silica gel (0.04–0.63 mm.) and eluted with toluene/diethyl ether (1:1). Similar fractions are combined and removed in vacuo to yield a colorless oil which is redissolved in 50 ml. diethyl ether and dry HCl bubbled in under a nitrogen atomsophere with stirring. The resulting white solid is filtered under a nitrogen atmosphere and dried in vacuo (0.1 mm.) for 24 hours at room temperature to yield 0.45 g. (44%) of the title product, m.p. 90°–95° C. (d).

NMR ($CDCl_3$) - 2.73 ppm. singlet, 3H (N—$CH_3$).
IR (KBr) - 4.25μ.

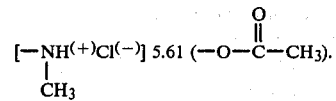

Calc'd. for $C_{28}H_{37}O_4N·HCl$: C, 68.90; H, 7.85; N, 2.87%; Found: C, 68.60; H, 7.92; N, 2.77%.
$[a]_D^{25} = -73°$ (C, 1.0, methanol).
Mass spectrum m/e=451 (m+).

EXAMPLE 13

Preparation of dl-5,6,6aβ,7,8,9α,10,10aα-octahydro-1-acetoxy-5-benzoyl-9-benzoyloxy-6β-methyl-3-(1-methyl-4-phenylbutoxy)benzo[c]quinoline A stirred suspension of 47.4 g. (0.10 mol) of dl-5,6,6aβ,7,8,9α,10,10aα-octahydro-1-acetoxy-9-hydroxy-6β-methyl-3-(1-methyl-4-phenylbutoxy)benzo[c]quinoline, hydrochloride and 500 ml. of $CHCl_3$ under a $N_2$ atmosphere is cooled to 0° C. and treated with 250 ml. pyridine followed by 58 ml. (0.50 mole) benzoyl chloride in 500 ml. chloroform. The resultant homogeneous solution is then refluxed on a steam bath for one hour. The reaction mixture is poured onto crushed ice and extracted with chloroform. The organic extracts are combined, washed successively with water (2×500 ml.), 10% hydrochloric acid, saturated sodium bicarbonate solution (500 ml.) and saturated brine solution (500 ml.), dried over $MgSO_4$, filtered and concentrated to give 119 g. of a light yellow oil. Chromatography on 2000 g. silica gel (20% EtOAc-cyclohexane) affords 50.5 g. (78%) of dl-5,6,6aβ,7,8,-,9α,10,10aα-octahydro-1-acetoxy-5-benzoyl-9-benzoyloxy-6β-methyl-3-(1-methyl-4-phenylbutoxy)benzo[c]quinoline, m.p. 125°–30° C.

Anal. Calc'd. for $C_{41}H_{43}O_6N$: C, 76.24; H, 6.72; N, 2.17%. Found: C, 76.35; H, 6.92; N, 2.19%.

Separation of dl-5,6,6aβ,7,8,9α,10,10aα-octahydro-1-acetoxy-5-benzoyl-9-benzoyloxy-6β-methyl-3-(1β-methyl-4-phenylbutoxy)benzo[c]quinoline and dl-5,6,6aβ,7,8,9α,10,10aα-octahydro-1-acetoxy-5-benzoyl-9-benzyloxy-6β-methyl-3-(1α-methyl-4-phenylbutoxy)-benzo[c]quinoline Recrystallization of 50.5 g. dl-5,6,6aβ,7,8,9α,10,10aα-octahydro-1-acetoxy-5-benzoyl-9-benzoyloxy-6β-methyl-3-(1-methyl-4-phenylbutoxy)benzo[c]quinoline from 2·1. 2-propanol yielded 23.8 of white solids, m.p. 136°–8°, which are recrystallized twice more from 2-propanol and once from acetonitrile to yield 5.7 g. of dl-5,6,6aβ,7,8,9α,10,10aα-octahydro-1-acetoxy-5-benzoyl-9-benzoyloxy-6β-methyl-3-(1β-methyl-4-phenylbutoxy)benzo[c]quinoline, m.p. 148°–9° C.

The filtrate from the original 2-propanol recrystallization of dl-5,6,6aβ,7,8,9α,10,10aα-octahydro-1-acetoxy-5-benzoyl-9-benzoyloxy-6β-methyl-3-(1-methyl-4-phenylbutoxy)benzo[c]quinoline is evaporated to a white foam and triturated with 500 ml. ether to yield 12.9 g. of white solids, m.p. 129°–132°. These solids are triturated twice again with ether to yield 3.8 g. of dl-5,6,6aβ,7,8,9α,10,10aα-octahydro-1-acetoxy-5-benzoyl-9-benzoyloxy-6β-methyl-3-(1α-methyl-4-phenylbutoxy)benzo[c]quinoline, m.p. 139°–141° C.

Preparation of
dl-5,6,6aβ,7,8,9α,10aα-octahydro-1-acetoxy-9-hydroxy-6β-methyl-3-(1β-methyl-4-phenylbutoxy)benzo[c]quinoline, hydrochloride To a stirred solution of 2.0 g. lithium aluminum hydride in 150 ml. tetrahydrofuran under a nitrogen atmosphere is added a solution of 5.7 g. (8.8 mmole) dl-5,6,6aβ,7,8,9α,10,10aα-octahydro-1-acetoxy-5-benzoyl-9-benzoyloxy-6β-methyl-3-(1β-methyl-4-phenylbutoxy)benzo[c]quinoline in 112 ml. tetrahydrofuran dropwise over a five minute period. The resultant mixture is heated at reflux for 45 minutes, cooled and poured carefully onto an ice cold mixture of 1125 ml. 5% acetic acid in water and 2250 ml. ether. This biphasic mixture is stirred for ten minutes and the layers separated. The aqueous layer is extracted with an additional 500 ml. ether and the combined ether extracts ae washed successively with water (3×500 ml.), saturated sodium bicarbonate solution (2×500 ml.) and saturated brine solution (1×500 ml.), dried over MgSO4, filtered and evaporated to yield 5.4 g. dl-5-benzyl-5,6,6aβ,7,8-,9α,10,10aα-octahydro-1,9-dihydroxy-6β-methyl-3-(1β-methyl-4-phenylbutoxy)benzo[c]quinoline as a light purple oil.

dl-5-benzyl-5,6,6aβ,7,8,9α,10,10aα-octahydro-1,9-dihydroxy-6β-methyl-3-(1β-methyl-4-phenylbutoxy)benzo[c]quinoline is immediately taken up in 450 ml. methanol and hydrogenated at atmospheric pressure over 4.27 g. Pd/C for 3 hours to yield dl-5,6,6aβ,7,8-,9α,10,10aα-octahydro-1,9-dihydroxy-6β-methyl-3-(1β-methyl-4-phenylbutoxy)benzo[c]quinoline after filtration of the catalyst and evaporation of the methanol.

dl-5,6,6aβ,7,8,9α,10,10aα-octahydro-1,9-dihydroxy-6β-methyl-3-(1β-methyl-4-phenylbutoxy)benzo[c]quinoline is immediately dissolved in 210 ml. methylene chloride, cooled to 0° C. under a nitrogen atmosphere, and treated successively with 1.35 ml. triethylamine, 1.19 g. (9.7 mmol) of 4-dimethylaminopyridine and finally with 0.834 ml. (8.8 mmol) of acetic anhydride. After stirring for 30 minutes, the reaction mixture is poured onto 250 ml. of water and the organic layer separated. The aqueous layer is extracted once more with methylene chloride and the combined methylene chloride layers washed successively with a saturated sodium bicarbonate solution (2×150 ml.), wate (150 ml.) and a saturated brine solution, dried over MgSO4, filtered, evaporated and chromatographed on 300 g. silica gel using 33% ether-toluene as eluent to give 1.4 g. dl-5,6,6aβ,7,8,9α,10,10aα-octahydro-1-acetoxy-9-hydroxy-6β-methyl-3-(1β-methyl-4-phenylbutoxy)benzo[c]quinoline, as the free base. Treatment of dl-5,6,6aβ,7,8,9α,10,10aα-octahydro-1-acetoxy-9-hydroxy-6β-methyl-3-(1β-methyl-4-phenylbutoxy)benzo[c]quinoline, in ether with HCl (gas) yields 795 mg. dl-5,6,6aβ,7,8,9α,-10,10aα-octahydro-1-acetoxy-9-hydroxy-6β-methyl-3-(1β-methyl-4-phenylbutoxy)benzo[c]quinoline, hydrochloride, m.p. 213°–215° C. after filtration and trituration in acetone, m/e=437 (m+, 100%).

Anal. Calc'd. for $C_{27}H_{35}O_4N \cdot HCl$: C, 68.42; H, 7.66; N, 2.96. Found: C, 68.48; H, 7.63; N, 3.05.

Similarly prepared from 3.8 g. dl-5,6,6aβ,7,8,9α,10,-10aα-octahydro-1-acetoxy-5-benzoyl-9-benzoyloxy-6β-methyl-3-(1α-methyl-4-phenylbutoxy)benzo[c]quinoline is 1.1 g. dl-5,6,6aβ,7,8,9α,10,10aα-octahydro-1-acetoxy-9-hydroxy-6β-methyl-3-(1α-methyl-4-phenylbutoxy)benzo[c]-quinoline hydrochloride, m.p. 202°–205° (d.), m/e=437 (100%, m+).

Anal. Calc'd. for $C_{27}H_{35}O_4N \cdot HCl$: C, 68.42; H, 7.66; N, 2.96. Found: C, 68.20; H, 7.56; N, 3.04.

EXAMPLE 14 d,l-trans-5,6,6aβ,7,8,9,10,10aα-octahydro-1-(4-N-piperidylbutyryloxy)-9-hydroxy-6β-methyl-3-(5-phenyl-2-pentyloxy)benzo[c]quinoline hydrochloride To a 25° C. solution of d,l-trans-5,6,6aβ,7,8,9,10,-10aα-octahydro-1,9-dihydroxy-6β-methyl-3-(5-phenyl-2-pentyloxy)-benzo[c]quinoline (1.0 g., 2.53 mmoles) in methylene chloride (20 ml.) is added 4-N-piperidylbutyric acid hydrochloride (0.524 g., 2.53 mmoles) and dicyclohexylcarbodiimide (0.573 g., 2.78 mmoles). The reaction mixture is stirred at 25° C. for 6 hours and then cooled for 12 hours and filtered. Evaporation of the filtrate and trituration of the residue with ether gives 1.3 g. of solid of the monohydrochloride salt.

IR (KBr): 2.95, 3.70, 5.65 (ester C=O), 6.13 and 6.27μ.

Preparative layer chromatography of a portion of this solid on 0.5 mm. thick silica gel and elution with 10% methanol-methylene dichloride affords the free base, d,l-trans-5,6,6aβ,7,8,9,10,10aα-octahydro-1-(4-N-piperidylbutyryloxy)-9-hydroxy-6β-methyl-3-(5-phenyl-2-pentyloxy)benzo[c]quinoline.

$^1$H NMR (60 MHz) $\delta_{CDCl_3}^{TMS}$ (ppm): 1.12 (d, J=7 Hz, C-3 side-chain methyl), 1.25 (d, J=6 Hz, C-6 methyl), 5.84 (s, two ArH) and 7.16 (s, 5H).

Treatment of this free base with excess hydrogen chloride in ether yield the dihydrochloride salt as a hygroscopic powder.

EXAMPLE 15 d,l-5,6,6a,7-Tetrahydro-1-(4-N-piperidyl-butyryloxy)-6β-methyl-3-(5-phenyl-2-pentyloxy)-benzo[c]quinolin-9(8H)-one hydrochloride To a 25° C. solution of d,l-5,6,6a,7-tetrahydro-1-hydroxy-6β-methyl-3-(5-phenyl-2-pentyloxy)benzo[c]-quinoline-9(8H)-one (550 mg., 1.41 mmole) in methylene chloride (26 ml.) is added 4-N-piperidylbutyric acid hydrochloride (291 mg., 1.41 mmole) and dicyclohexylcarbodiimide (319 mg., 1.55 mmole). This reaction mixture is stirred for 18 hours and is then cooled to 0° C. and filtered. Evaporation of the filtrate and trituration of the residue with ether gives 800 mg. of d,l-5,6,6a,7-tetrahydro-1-(4-N-piperidylbutyryloxy)-6β-methyl-3-(5-phenyl-2-pentyloxy)benzo[c]quinoline-9(8H)-one hydrochloride as a hygroscopic yellow powder.

IR (CHCl3): 2.92, 4.14 (HN⊕=), 5.69 (ester), 6.00, 6.20 and 6.40μ.

In like manner, d,l-trans-5,6,6aβ,7,8,9,10,10aα-octahydro-1-(4-N-morpholinobutyryloxy)-9-hydroxy-6β-methyl-3-(5-phenyl-2-pentyloxy)benzo[c]quinoline hydrochloride is prepared from 4-N-morpholinobutyric acid and d,l-trans-5,6,6aβ,7,8,9,10,10aα-octahydro-1,9-dihydroxy-6β-methyl-3-(5-phenyl-2-pentyloxy)benzo[c]-quinoline:

IR (KBr): 3.00, 3.75, 5.67 (ester C=O), 6.15 and 6.30μ.

EXAMPLE 16

General Hydrochloride Salt Formation

Excess hydrogen chloride is passed into a solution of the appropriate benzo[c]quinoline of formulae I and II and the resulting precipitate separated and recrystallised from an appropriate solvent, e.g. methanol-ether (1:10).

In this manner the following salt is prepared:
d,l-trans-5,6,6a$\beta$,7,8,9,10,10a$\alpha$-octahydro-1-acetoxy-9$\beta$-hydroxy-6$\beta$-methyl-3-(5-phenyl-2-pentyloxy)-benzo[c]quinoline, m.p. 191°–193° C.

m/e-437 (m+).

Analysis: Calc'd. for $C_{27}H_{36}O_4NCl$: C, 68.48; H, 7.70; N, 2.89%; Found: C, 68.42; H, 7.66; N, 2.96%.

We claim:

1. A process for the prevention and treatment of nausea in a mammal subject to said nausea which comprises administering to said mammal a compound in an amount effective to prevent nausea, said compound being selected from the group consisting of

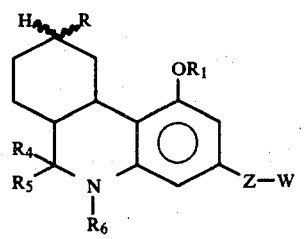

and the pharmaceutically acceptable acid addition salts thereof.

wherein R is selected from the group consisting of hydroxy and alkanoyloxy having from one to five carbon atoms;

$R_1$ is selected from the group consisting of hydrogen, benzyl, benzoyl, alkanoyl having from one to five carbon atoms and $-CO-(CH_2)_p-NR_2R_3$ wherein p is 0 or an integer from 1 to 4; each of $R_2$ and $R_3$ when taken individually is selected from the group consisting of hydrogen and alkyl having from one to four carbon atoms; $R_2$ and $R_3$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

$R_4$ is selected from the group consisting of hydrogen, alkyl having from 1 to 6 carbon atoms and $-(CH_2)_z-C_6H_5$ wherein z is an integer from 1 to 4;

$R_5$ is selected from the group consisting of hydrogen, methyl and ethyl;

$R_6$ is selected from the group consisting of hydrogen, $-(CH_2)_y$-carbalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms and $-(CH_2)_x-C_6H_5$ wherein x is an integer from 1 to 4; and $CO(CH_2)_{x-1}-C_6H_5$;

Z is selected from the group consisting of
(a) alkylene having from one to nine carbon atoms;
(b) $-(alk_1)_m-X-(alk_2)_n-$ wherein each of $(alk_1)$ and $(alk_2)$ is alkylene having from one to nine carbon atoms, with the proviso that the summation of carbon atoms in $(alk_1)$ plus $(alk_2)$ is not greater than nine; each of m and n is 0 or 1; X is selected from the group consisting of O, S, SO and $SO_2$; and W is selected from the group consisting of hydrogen, methyl, pyridyl, piperidyl,

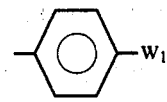

wherein $W_1$ is selected from the group consisting of hydrogen, fluoro and chloro; and

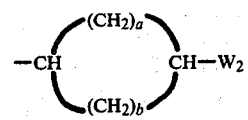

wherein $W_2$ is selected from the group consisting of hydrogen and

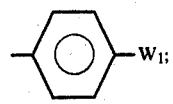

a is an integer from 1 to 5 and b is 0 or an integer from 1 to 5; with the proviso that the sum of a and b is not greater than 5.

2. A process according to claim 1 in which a compound wherein $R_1$ is hydrogen or alkanoyl; R is hydroxy or alkanoyloxy; $R_5$ is methyl or hydrogen; and each of $R_4$ and $R_6$ is hydrogen or alkyl is administered.

3. A process according to claim 2 in which a compound wherein $R_1$ is hydrogen or acetyl; R is hydroxy or acetoxy; Z is $-(alk_1)_m-X-(alk_2)_n-$ and W is hydrogen or phenyl is administered.

4. A process according to claim 3 in which a compound wherein Z is $-(alk_1)_m-O-(alk_2)_n-$ is administered.

5. A process according to claim 4 in which a compound wherein Z is $-O-(alk_2)-$, W is phenyl, $R_1$ is acetyl and R is hydroxy is administered.

6. A process according to claim 5 in which a trans-(6a,10a)diastereomer compound wherein Z is $-OCH(CH_3)(CH_2)_3-$ is administered.

7. A process according to claim 6 in which the compound wherein R is $\beta$-hydroxy; $R_1$ is acetyl; $R_4$ is $\beta$-methyl; and each of $R_5$ and $R_6$ is hydrogen is administered.

8. A process according to claim 6 in which the compound wherein R is $\beta$-hydroxy; $R_1$ is acetyl; $R_5$ is hydrogen; $R_6$ is methyl; and $R_4$ is $\beta$-methyl is administered.

9. A process according to claim 7 wherein (2'R,6S,6aR,9R,10aR)-(−)-1-acetoxy-5,6,6a,7,8,9,10,-10a-octahydro-9-hydroxy-6-methyl-3-(5'-phenyl-2'-pentyloxy)-benzo[c]quinoline hydrochloride, a single stereoisomer according to claim 7 is administered.

10. A process according to claim 8 wherein (2'R,6S,6aR,9R,10aR)-(−)-1-acetoxy-5,6,6a,7,8,9,10,-10a-octahydro-9-hydroxy-5,6-dimethyl-3-(5'-phenyl-2'pentyl-oxy)benzo[c]quinoline hydrochloride, a single stereoisomer according to claim 8 is administered.

11. A process according to claim 6 in which a compound wherein R is β-hydroxy; $R_1$ is acetyl; each of $R_4$ and $R_5$ is methyl; and $R_6$ is hydrogen is administered.

12. A process according to claim 6 in which a compound wherein R is β-hydroxy; $R_1$ is acetyl; each of $R_4$ and $R_5$ is hydrogen; and $R_6$ is methyl is administered.

13. A process according to claim 1 in which a compound wherein $R_1$ is hydrogen or acetyl; R is hydroxy or acetoxy; Z is -alkylene-; and W is hydrogen or phenyl is administered.

14. A process according to claim 13 in which a compound wherein $R_1$ is acetyl; R is hydroxy; and W is hydrogen is administered.

15. A process according to claim 14 in which a compound wherein $R_5$ is hydrogen; and each of $R_4$ and $R_6$ is methyl is administered.

16. A process according to claim 15 in which the compound wherein R is β-hydroxy; $R_4$ is β-methyl; and Z is $-C(CH_3)_2(CH_2)_6-$ is administered.

17. A process according to claim 13 in which the compound wherein $R_1$ is acetyl; R is β-hydroxy; W is phenyl; each of $R_5$ and $R_6$ is hydrogen; $R_4$ is β-methyl; and Z is $-CH(CH_3)(CH_2)_3-$ is administered.

18. A process for the prevention and treatment of nausea in a mammal subject to said nausea which comprises administering to said mammal a compound in an amount effective to prevent nausea, said compound being selected from the group consisting of:

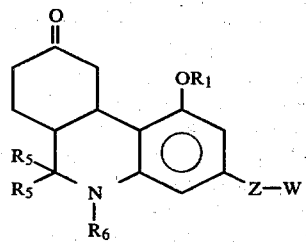

and the pharmaceutically acceptable acid addition salts thereof wherein $R_1$ is selected from the group consisting of hydrogen, benzyl, benzoyl, alkanoyl having from one to five carbon atoms and $-CO-(CH_2)_p-NR_2R_3$ wherein p is 0 or an integer from 1 to 4; each of $R_2$ and $R_3$ when taken individually is selected from the group consisting of hydrogen and alkyl having from one to four carbon atoms; $R_2$ and $R_3$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

$R_4$ is selected from the group consisting of hydrogen, alkyl having from 1 to 6 carbon atoms and $-(CH_2)_z-C_6H_5$ wherein z is an integer from 1 to 4;

$R_5$ is selected from the group consisting of hydrogen, methyl and ethyl;

$R_6$ is selected from the group consisting of hydrogen, $-(CH_2)_y-$carbalkoxy having from one to four carbon atoms in the alkoxy group and wherein y is 0 or an integer from 1 to 4; carbobenzyloxy, formyl, alkanoyl having from two to five carbon atoms, alkyl having from one to six carbon atoms;

$-(CH_2)_x-C_6H_5$ wherein x is an integer from 1 to 4; and $-CO(CH_2)_{x-1}-C_6H_5$;

Z is selected from the group consisting of
(a) alkylene having from one to nine carbon atoms;
(b) $-(alk_1)_m-X-(alk_2)_n-$ wherein each of $(alk_1)$ and $(alk_2)$ is alkylene having from one to nine carbon atoms, with the proviso that the summation of carbon atoms in $(alk_1)$ plus $(alk_2)$ is not greater than nine; each of m and n is 0 or 1; X is selected from the group consisting of O, S, SO and $SO_2$; and W is selected from the group consisting of hydrogen, methyl, pyridyl, piperidyl,

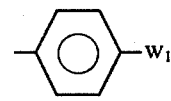

wherein $W_1$ is selected from the group consisting of hydrogen, fluoro and chloro; and

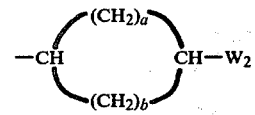

wherein $W_2$ is selected from the group consisting of hydrogen and

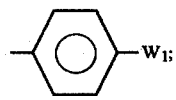

a is an integer from 1 to 5 and b is 0 or an integer from 1 to 5; with the proviso that the sum of a and b is not greater than 5.

19. A process according to claim 18 in which a compound wherein $R_5$ is hydrogen or methyl; each of $R_4$ and $R_6$ is hydrogen or alkyl; $R_1$ is hydrogen or alkanoyl; Z is $-(alk_1)_m-O-(alk_2)_n-$; and W is phenyl or hydrogen is administered.

20. A process according to claim 19 in which a compound wherein $R_4$ is β-methyl; $R_1$ is acetyl; each of $R_5$ and $R_6$ is hydrogen; Z is $-O-(alk_2)_n-$; and W is phenyl is administered.

21. A process according to claim 20 in which the compound wherein Z is $-O-CH(CH_3)(CH_2)_3-$ is administered.

22. A process according to claim 21 in which the trans(6a,10a)diastereomer is administered.

23. A process according to claim 21 in which the cis(6a,10a)diastereomer is administered.

24. A process according to claim 18 wherein $R_1$ is hydrogen or acetyl; each of $R_4$, $R_5$ and $R_6$ is hydrogen or methyl; Z is -alkylene-; and W is hydrogen or phenyl.

25. A process according to claim 24 in which a compound wherein Z is $-C(CH_3)_2(CH_2)_6-$ and W is hydrogen is administered.

26. A process according to claim 25 in which the compound wherein $R_1$ is acetyl, each of $R_5$ and $R_6$ is hydrogen and $R_4$ is β-methyl is administered.

27. A process according to claim 25 in which the compound wherein $R_1$ is acetyl, $R_5$ is hydrogen, $R_4$ is β-methyl and $R_6$ is methyl is administered.

* * * * *

UNITED STATES PATENT AND TRADEMARK OFFICE
CERTIFICATE OF CORRECTION

PATENT NO. : 4,228,169
DATED : October 14, 1980
INVENTOR(S) : MICHAEL R. JOHNSON ET AL It is certified that error appears in the above-identified patent and that said Letters Patent are hereby corrected as shown below:

In the ABSTRACT, " 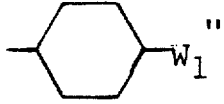 " should read

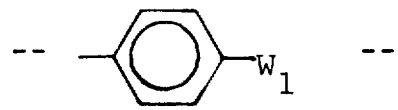

In the ABSTRACT, " 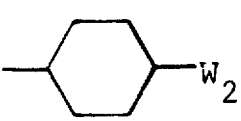 " should read

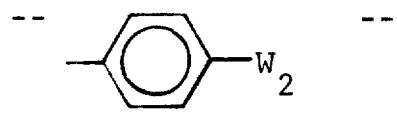

UNITED STATES PATENT AND TRADEMARK OFFICE
CERTIFICATE OF CORRECTION

PATENT NO. : 4,228,169
DATED : October 14, 1980
INVENTOR(S) : MICHAEL R. JOHNSON ET AL It is certified that error appears in the above-identified patent and that said Letters Patent are hereby corrected as shown below:

In the ABSTRACT, formula I should read

-- 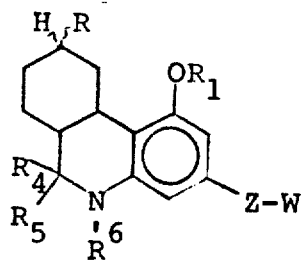 --

In the ABSTRACT, formula II should read

-- 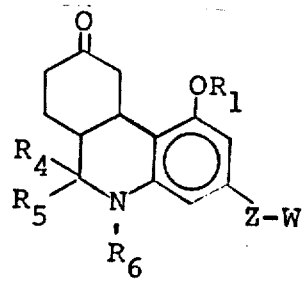 --

UNITED STATES PATENT AND TRADEMARK OFFICE
CERTIFICATE OF CORRECTION

PATENT NO. : 4,228,169

DATED : October 14, 1980

INVENTOR(S) : MICHAEL R. JOHNSON ET AL

It is certified that error appears in the above-identified patent and that said Letters Patent are hereby corrected as shown below:

Column 10, line 50, "also" should read -- into --

Column 13, line 64, "guinolin" should read --quinolin--.

Signed and Sealed this

Twenty-seventh Day of January 1981

[SEAL]

Attest:

Attesting Officer

RENE D. TEGTMEYER

Acting Commissioner of Patents and Trademarks